United States Patent
Newsome et al.

(10) Patent No.: US 8,308,811 B2
(45) Date of Patent: *Nov. 13, 2012

(54) ACETABULAR CUP CONVERSION RING

(75) Inventors: Archie W. Newsome, Mentone, IN (US);
Randy L. Schlemmer, Bremen, IN
(US); Erin M. Johnson, Columbia City,
IN (US); Richard A. Berger, Chicago,
IL (US)

(73) Assignee: Zimmer, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/751,330

(22) Filed: Mar. 31, 2010

(65) Prior Publication Data

US 2011/0087335 A1    Apr. 14, 2011

Related U.S. Application Data

(60) Continuation-in-part of application No. 12/504,155, filed on Jul. 16, 2009, now Pat. No. 7,985,259, which is a division of application No. 11/401,727, filed on Apr. 11, 2006, now abandoned.

(60) Provisional application No. 61/165,591, filed on Apr. 1, 2009.

(51) Int. Cl.
*A61F 2/32* (2006.01)

(52) U.S. Cl. ............... 623/22.21; 623/22.24; 623/22.25; 623/22.26; 623/22.3

(58) Field of Classification Search ............... 623/22.21, 623/24, 25, 26, 19, 22, 21, 3
See application file for complete search history.

(56) References Cited

U.S. PATENT DOCUMENTS

| | | | |
|---|---|---|---|
| 2,339,771 | A | 1/1944 | Davies |
| 2,900,292 | A | 8/1959 | Coleman, Jr. et al. |
| 3,179,448 | A | 4/1965 | Jones |
| 3,683,421 | A | 8/1972 | Martinie |
| 3,903,549 | A | 9/1975 | Deyerle |
| 3,978,528 | A | 9/1976 | Crep |
| 4,058,024 | A | 11/1977 | Gordon |
| 4,355,825 | A | 10/1982 | Leicht |
| 4,642,123 | A | 2/1987 | Noiles |
| 4,678,472 | A | 7/1987 | Noiles |

(Continued)

FOREIGN PATENT DOCUMENTS

EP    0086879 A1    8/1983

(Continued)

OTHER PUBLICATIONS

Webpage—Zimmer Product—Epsilon Durasul Constrained Insert, 3 pages, 2007 Zimmer, Inc. (EpsilonDurasul).

(Continued)

*Primary Examiner* — Bruce E Snow
*Assistant Examiner* — Brian Dukert
(74) *Attorney, Agent, or Firm* — Schwegman, Lundberg & Woessner, P.A.

(57) ABSTRACT

An acetabular implant for hip replacement surgery includes a shell component and first and second alternative bearing components interchangeably engageable with the shell component to provide a choice in bearing components. The shell component has a shell component engagement mechanism suitable for engaging the first alternative bearing component. A conversion ring is also engageable with the shell component, so that a shell component/conversion ring assembly provides a second shell component engagement mechanism suitable for engagement with the second alternative bearing component.

20 Claims, 6 Drawing Sheets

U.S. PATENT DOCUMENTS

| | | | |
|---|---|---|---|
| 4,770,658 | A | 9/1988 | Geremakis |
| 4,813,963 | A | 3/1989 | Hori et al. |
| 4,886,113 | A | 12/1989 | Ross et al. |
| 5,092,897 | A | 3/1992 | Forte |
| 5,104,399 | A | 4/1992 | Lazarus |
| 5,282,864 | A | 2/1994 | Noiles et al. |
| 5,310,408 | A | 5/1994 | Schryver et al. |
| 5,314,491 | A | 5/1994 | Thongpreda et al. |
| 5,362,311 | A | 11/1994 | Amino et al. |
| 5,383,938 | A | 1/1995 | Rohr et al. |
| 5,392,596 | A | 2/1995 | Nolsapple et al. |
| 5,507,824 | A | 4/1996 | Lennox |
| 5,549,691 | A | 8/1996 | Harwin |
| 5,549,701 | A | 8/1996 | Mikhail |
| 5,593,445 | A | 1/1997 | Waits |
| 5,725,591 | A | 3/1998 | DeCarlo et al. |
| 5,824,108 | A | 10/1998 | Huebner |
| 5,938,698 | A | 8/1999 | Sandoz et al. |
| 5,989,294 | A | 11/1999 | Marlow |
| 6,217,832 | B1 | 4/2001 | Betta et al. |
| 6,231,612 | B1 | 5/2001 | Balay et al. |
| 6,328,764 | B1 | 12/2001 | Mady |
| 6,475,243 | B1 * | 11/2002 | Sheldon et al. ............ 623/22.28 |
| 6,527,808 | B1 | 3/2003 | Albertorio et al. |
| 6,589,284 | B1 | 7/2003 | Silberer |
| 6,610,097 | B2 | 8/2003 | Serbousek et al. |
| 6,620,200 | B1 | 9/2003 | Descamps et al. |
| 6,827,742 | B2 | 12/2004 | Hayes et al. |
| 6,916,342 | B2 | 7/2005 | Frederick |
| 6,976,999 | B2 | 12/2005 | Charlebois et al. |
| 7,040,407 | B2 | 5/2006 | Jennings et al. |
| 7,115,145 | B2 | 10/2006 | Richards |
| 7,208,222 | B2 | 4/2007 | Rolfe et al. |
| 2001/0037156 | A1 | 11/2001 | Burstein et al. |
| 2002/0068980 | A1 | 6/2002 | Serbousek et al. |
| 2003/0050703 | A1 | 3/2003 | Harris et al. |
| 2003/0105529 | A1 | 6/2003 | Synder et al. |
| 2003/0187512 | A1 | 10/2003 | Frederick et al. |
| 2005/0004677 | A1 | 1/2005 | Johnson |
| 2005/0004678 | A1 | 1/2005 | Richards |
| 2005/0102034 | A1 | 5/2005 | Hayes et al. |
| 2005/0240276 | A1 | 10/2005 | Shea et al. |
| 2006/0149256 | A1 | 7/2006 | Wagner et al. |
| 2006/0226570 | A1 | 10/2006 | Brown et al. |
| 2006/0241781 | A1 | 10/2006 | Brown et al. |
| 2007/0106390 | A1 | 5/2007 | Richards |
| 2007/0239283 | A1 | 10/2007 | Berger |

FOREIGN PATENT DOCUMENTS

| | | |
|---|---|---|
| EP | 0694294 A1 | 1/1996 |
| EP | 0773007 A1 | 5/1997 |
| FR | 2357235 A1 | 2/1978 |
| FR | 2684544 A1 | 6/1993 |
| FR | 2805151 A1 | 8/2001 |
| FR | 2824258 A1 | 11/2002 |
| GB | 2306330 A | 5/1999 |
| WO | WO00/64383 A1 | 11/2002 |

OTHER PUBLICATIONS

Office Action mailed Jun. 18, 2007, in U.S. Appl. No. 11/104,351.

Wright Medical Technology, Inc. "Lineage Acetabular Cup System Surgical Technique," copyright 2003, Arlington, TN 38002 (12 pages) (LineageCeramicST).

ISR and WO issued in related International App. No. PCT/US2007/066309 on Aug. 23, 2007.

* cited by examiner

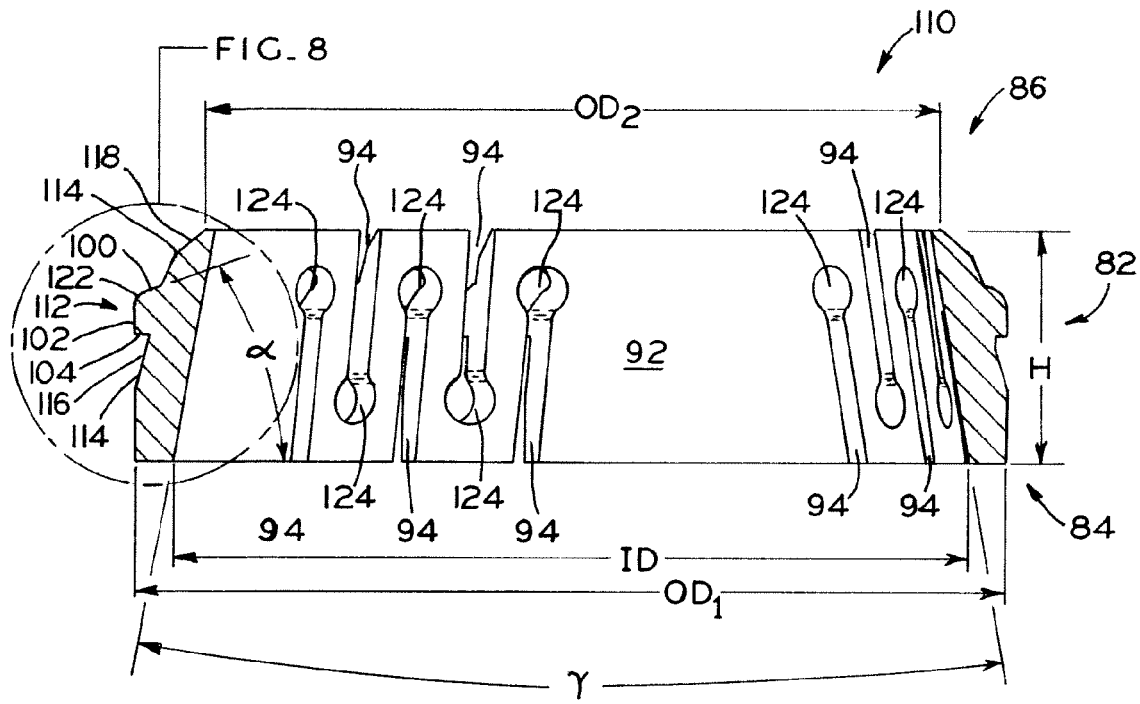
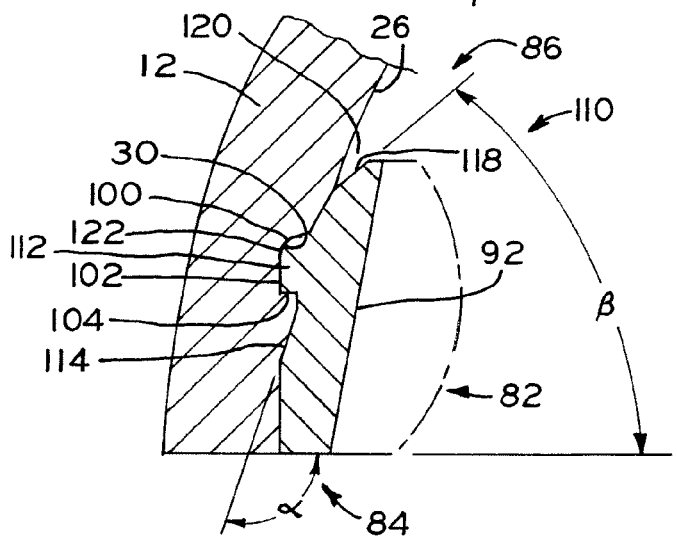

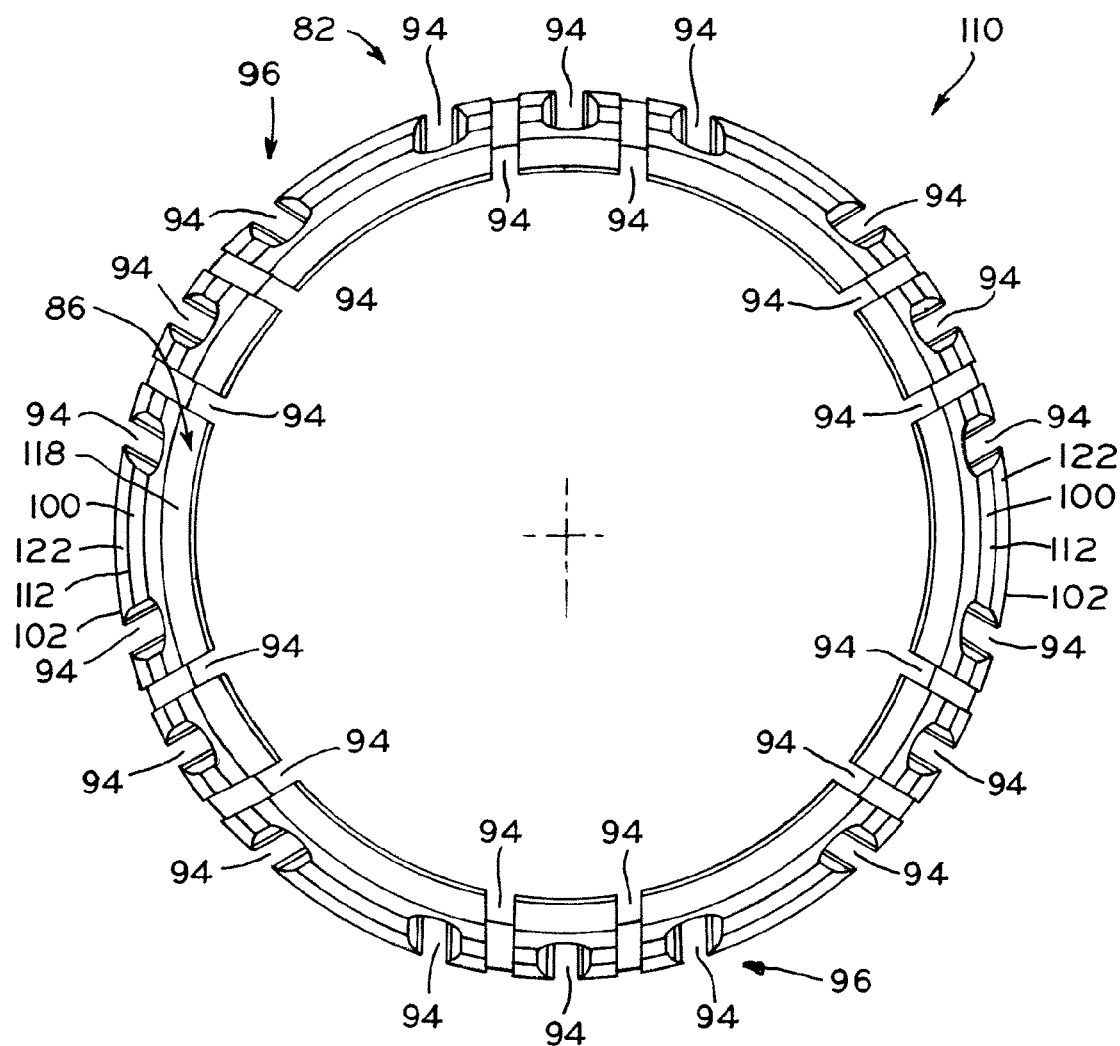
FIG_9

ACETABULAR CUP CONVERSION RING

CROSS REFERENCE TO RELATED APPLICATIONS

This application claims the benefit under Title 35, U.S.C. §119(e) of U.S. Provisional Patent Application Ser. No. 61/165,591, entitled ACETABULAR CUP CONVERSION RING and filed on Apr. 1, 2009, the entire disclosure of which is expressly incorporated herein by reference.

This application is a continuation-in-part of U.S. patent application Ser. No. 12/504,155, entitled ACETABULAR CUP CONVERSION RING which was filed on Jul. 16, 2009 and issued as U.S. Pat. No. 7,985,259 on Jul. 26, 2011, which is a divisional of U.S. patent application Ser. No. 11/401,727, entitled ACETABULAR CUP CONVERSION RING and filed on Apr. 11, 2006 now abandoned, the entire disclosures of which are expressly incorporated herein by reference.

BACKGROUND

1. Technical Field

The present disclosure relates to acetabular implants for hip replacement surgery. In particular, the present disclosure relates to acetabular implants including a shell component and alternative bearing components interchangeably engageable with the shell component to provide a choice of bearing materials.

2. Description of the Related Art

Total hip replacement surgery is commonly performed to alleviate pain and loss of function in injured or diseased hip joints. During this surgery, the articulating surfaces of the hip joint are replaced with prosthetic bearing components. The replacement components generally include a femoral component having a convex bearing surface and an acetabular cup component having a mating concave bearing surface.

Modular prosthetic components have become popular because they allow the surgeon to assemble components in a variety of configurations at the time of surgery to meet specific patient needs and surgeon preferences. For example, modular acetabular components generally include separate shell and liner components that can be assembled in a variety of configurations of shell surface finish, shell outer diameter, liner inner diameter, and liner bearing material. With a modular acetabular component, it is desirable to lock the shell and liner together to prevent expulsion of the liner and to minimize debris producing wear between them. Typically, the engagement mechanism is formed adjacent the equator of a hemispherical shell and liner to maximize the engagement area and the resulting holding power of the engagement mechanism.

Various liner bearing materials are in use. The liners vary in hardness, friction coefficient with different paired ball heads, weight, and wear resistance. Polymers, including ultrahigh molecular weight polyethylene (UHMWPE), are commonly used as bearing materials paired with an opposing metal, ceramic, or other composition ball head. The wear resistance of UHMWPE has been improved by irradiating it to cause changes in its chemical and mechanical properties. As the wear properties are improved, the bulk physical properties also change. Other materials, including metals and ceramics, have also been used for acetabular bearings. These materials vary from one another in terms of their hardness, resilience, brittleness, and other physical properties. Because of this variation, various mechanisms have been developed for engaging acetabular liners with their mating shells. Different engagement mechanisms are suitable for different liner and shell material combinations. These engagement mechanisms include snap-fit, cylindrical press-fit, taper-fit, threaded engagement, and other suitable locking mechanisms. It is desirable to be able to alternately fit different liners into a common shell to reduce inventory while allowing surgeon choice in liner selection. It is also desirable to allow intraoperatively changing from one liner to another without having to remove a shell that has already been placed in the surgical site during a primary surgery, or one that has become well fixed and only needs liner replacement in a revision surgery.

U.S. Pat. No. 6,475,243 issued to Sheldon et al. on Nov. 5, 2002 (the "'243 patent"). The '243 patent discloses an acetabular cup assembly that allows pre-operative or interoperative selection and securement of a bearing member within a shell member. The shell is metallic, while the bearing insert is in the form of a plastic bearing member. The assembly of the '243 patent includes a securing mechanism including an annular recess formed in the shell and a complementary annular rib that seats within the annular recess. In this assembly, the preferred material for the bearing member is polyethylene.

Alternatively, the '243 patent discloses a sleeve that may be secured within the shell by locking of tapered seating surfaces. A bearing member is secured to the sleeve with a tapered securement surface. The preferred material for the sleeve is commercially pure titanium. A recess may be formed in the tapered seating surface so that engagement of tapered seating surfaces occurs along two segments having generally the same axial length.

U.S. Pat. No. 6,610,097 issued to Serbousek et al. on Aug. 26, 2003 (the "'097 patent"). The '097 patent discloses a shell, a liner and a bearing. The bearing is coupled to the liner to form a subassembly by cooling the bearing, such as with liquid nitrogen, to shrink the size of the bearing, then press-fitting the bearing into the liner and allowing the bearing to warm and return to a larger size. The bearing and liner are fastened together in a fixed and locked position to form the bearing/liner subassembly. The liner provides a metal taper surface that forms a metal-to-metal locking connection between the subassembly and the shell.

SUMMARY

The present disclosure provides an acetabular implant for hip replacement surgery including a shell component and first and second alternative bearing components interchangeably engageable with the shell component to provide a choice in bearing components. The shell component has a shell component engagement mechanism suitable for engaging the first alternative bearing component. A conversion ring is also engageable with the shell component, so that a shell component/conversion ring assembly provides a second shell component engagement mechanism suitable for engagement with the second alternative bearing component.

In one form thereof, the present invention provides an acetabular prosthesis comprising: a shell component having a convex external surface shaped for engagement with an acetabulum and a concave interior surface defining an internal cavity, the interior surface including an annular groove; a first bearing component having a convex external surface and a concave internal surface, the external surface defining an annular projection configured for receipt within the annular groove of the shell component in mating snap-fit engagement; a conversion ring having a sidewall defining an outer surface and a tapered inner surface, the sidewall extending axially from a first end to a second end, the outer surface defining an annular projection configured for receipt within the annular groove of the shell component in mating snap-fit engagement; and a second bearing component having a tapered external surface and a concave internal surface, the external surface configured to releasably engage the tapered internal surface of the conversion ring in mating taper-fit engagement.

In another form thereof, the present invention provides a kit of acetabular components for assembling an acetabular joint prosthesis including a shell component and a bearing component disposed in the shell component, the kit comprising: a shell component having an external surface shaped for engagement with an acetabulum and an internal cavity, the cavity including a shell component engagement mechanism; a first bearing component having an external surface, the external surface defining a complimentary first bearing engagement mechanism engageable with the shell component engagement mechanism; a conversion ring having a sidewall defining an outer surface and an inner surface and extending axially from a first end to a second end, the outer surface defining a complimentary outer ring engagement mechanism releasably engageable with the shell component engagement mechanism, the inner surface defining an inner ring engagement mechanism; a second bearing component having an external surface, the external surface defining a complimentary second bearing engagement mechanism releasably engageable with the inner ring engagement mechanism, such that the conversion ring is insertable into the shell component to convert the shell component from a first shell/bearing engagement mechanism to a second shell/bearing engagement mechanism, the first and second shell/bearing engagement mechanisms being of different types selected from the group consisting of snap-fit, press-fit, taper-fit, and threaded-fit engagement mechanisms.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 7 is a cross-sectional view of the conversion ring of FIG. 6 taken along line 7-7 of FIG. 6;

FIG. 8 is an enlarged, fragmentary view of the conversion ring of FIG. 7 showing a section of the conversion ring positioned within an acetabular shell; and FIG. 9 is a plan view of another exemplary embodiment of an acetabular cup conversion ring.

Corresponding reference characters indicate corresponding parts throughout the several views. The exemplifications set out herein illustrate exemplary embodiments of the invention, and such exemplifications are not to be construed as limiting the scope of the invention in any manner.

DESCRIPTION OF THE ILLUSTRATIVE EXAMPLES

Figure 1:
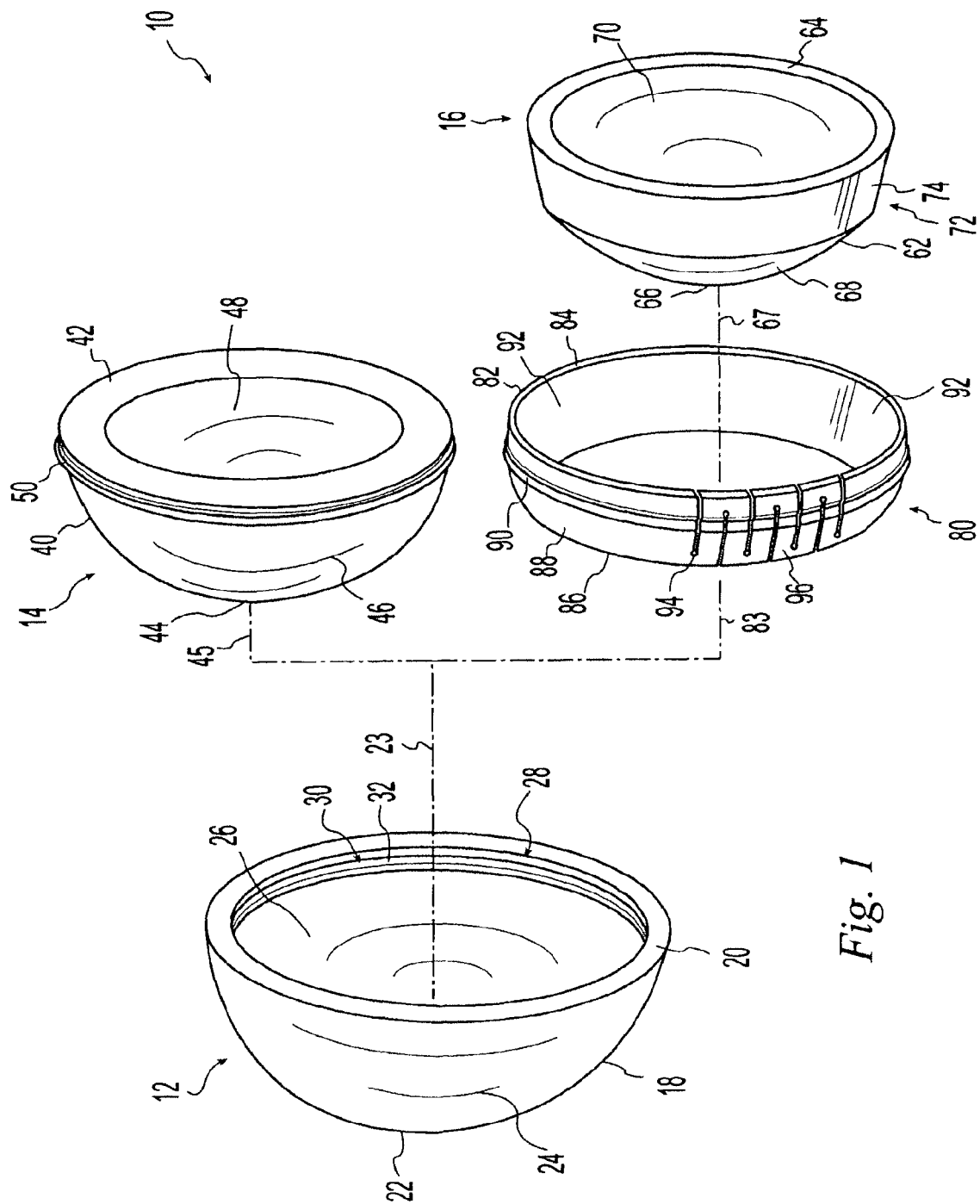
FIG. 1 is a perspective view of an illustrative exemplary kit of acetabular components for assembling alternative acetabular hip implants.

Embodiments of the present disclosure include an acetabular cup conversion ring engageable with an acetabular shell component. The shell component includes a shell component engagement mechanism for engaging a first alternative bearing component to couple it to the shell component. Alternatively, the conversion ring may be engaged with the shell component engagement mechanism to convert the shell component from being engageable with the first alternative bearing component via a first shell/bearing engagement mechanism to being engageable with the second alternative bearing component via a second shell/bearing engagement mechanism. Thus, the conversion ring facilitates the pairing of a variety of bearing components with a common acetabular shell component, by converting a first shell/bearing engagement mechanism to a second alternative shell/bearing engagement mechanism suitable for use with an alternative bearing component. For example, alternative bearing components may be provided that differ in material, size, shape, and/or other parameters, and may be made from a variety of materials such as polyethylene, crosslinked polyethylene, metal, ceramic, and/or other suitable materials. In addition, the first and second shell/bearing engagement mechanisms may be of a common type or a different type, including snap-fit, press-fit, taper-fit, threaded-fit, and the like.

The conversion ring may be closed at one end or it may be open at both ends to permit the bearing component to extend through the ring. This allows the bearing component to occupy the full depth of the shell component and thereby maximize the bearing thickness at a polar region of the bearing component. The conversion ring may be generally in the form of a hollow ring or band. The conversion ring may include an outer ring engagement mechanism formed on its outer surface that is engageable with the shell component engagement mechanism formed on the inside of the shell. The conversion ring may include an inner ring engagement mechanism formed on its inner surface that is engageable with the second bearing engagement mechanism formed on an alternative bearing component.

The first and second bearing engagement mechanisms, and the corresponding shell component and inner conversion ring engagement mechanisms, may be of the same or a different type. Engagement mechanism types may include snap-fit, press-fit, taper-fit, threaded, and/or other suitable engagement mechanism types. The inner conversion ring engagement mechanism may be configured for a particular type of bearing component. In addition, multiple conversion rings may be provided in a variety of configurations to adapt a variety of different bearing components to a common shell. For example, the shell component engagement mechanism may provide a snap-fit to engage a relatively resilient bearing component directly in the shell. A relatively rigid alternative bearing component may be more suited to a taper-fit engagement mechanism. In this example, the conversion ring would include a complimentary snap-fit engagement mechanism on its outer surface engageable with the shell, and a complimentary taper-fit engagement mechanism on its inner surface engageable with the alternative bearing component. In another example, the shell component engagement mechanism may include a taper-fit suited to the first bearing component, while the second bearing component may utilize a taper-fit having a different taper angle. In this example, the conversion ring would have a taper-fit on both its inner and outer surfaces, with the angle of the outer surface different from the angle of the inner surface to accommodate the differing taper-fits of the shell component engagement mechanism and the second bearing engagement mechanism.

The conversion ring may be made of a variety of materials including polymers, metals, ceramics, and combinations thereof. Where a snap-fit engagement mechanism is employed for one of the cooperating pairs of engagement mechanisms, a degree of resiliency is desirable to facilitate the snap-fit function. The conversion ring, or at least the snap-fit portion of the conversion ring, may be made of a relatively resilient material to facilitate the snap fit.

Alternatively, the conversion ring may be made of a relatively rigid material that is shaped to impart resiliency to selected portions of the ring. For example, the conversion ring may be made of a relatively rigid metal with a portion of the ring being removed to allow the ring to compress and expand to function in a snap-fit engagement mechanism. For example the conversion ring may be cut through its sidewall to allow the ring to compress to a smaller diameter. In another example, the ring sidewall may remain a continuous band but may include multiple cuts extending part-way through the sidewall and originating on alternating opposite sides to form at least a portion of the sidewall into a serpentine sidewall that is more resilient than the remaining uncut sidewall.

Figure 2:
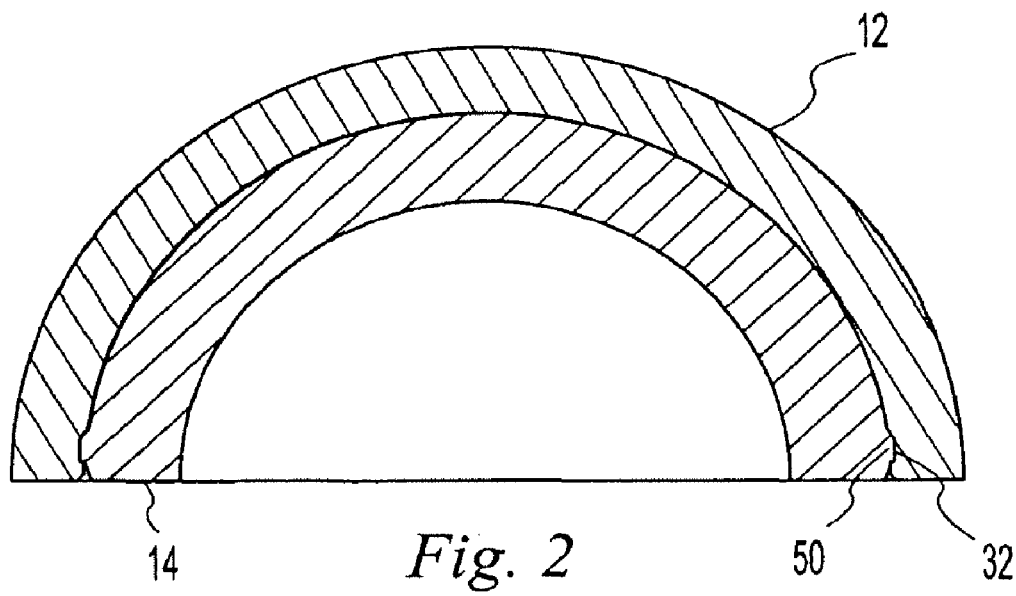
FIG. 2 is a cross sectional view of one illustrative alternative acetabular hip component assembled from the kit of FIG. 1.
Figure 3:
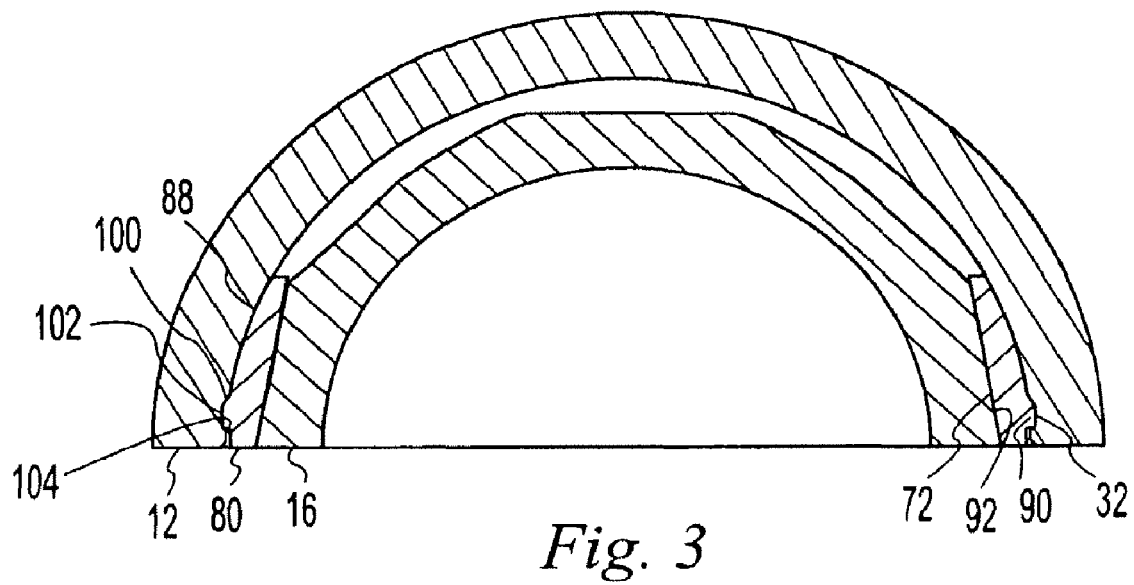
FIG. 3 is a cross sectional view of another illustrative alternative acetabular hip component assembled from the kit of FIG. 1.

Turning now to the illustrated embodiments, FIGS. 1-3 depict acetabular cup assembly 10 including shell component 12 and alternative first and second bearing components 14, 16. Shell component 12 includes hollow hemispherical body 18 extending from equatorial rim 20 to polar end 22 along axis 23 and defining convex exterior surface 24 and concave interior surface 26. Rim 20 defines circular opening 28 communicating with interior surface 26. Shell component engagement mechanism 30, in the form of a snap-fit engagement mechanism, is formed on interior surface 26 adjacent rim 20. In one exemplary embodiment, shell component engagement mechanism 30 includes annular groove 32 formed into body 18.

First bearing component 14 includes hollow hemispherical body 40 extending from equatorial rim 42 to polar end 44 along axis 45 and defining convex exterior surface 46 and concave interior surface 48. First bearing component 14 includes a complimentary snap-fit first bearing engagement mechanism including annular projection 50 sized to fit within annular groove 32 of shell component 12. When first bearing component 14 is pressed into shell component 12, annular projection 50 deforms resiliently to fit through opening 28 and snaps into groove 32 to retain first bearing component 14 in shell component 12. In one exemplary embodiment, first bearing component 14 is made of polyethylene.

Second bearing component 16 includes hollow hemispherical body 62 extending from equatorial rim 64 to polar end 66 along axis 67 and defining convex exterior portion 68 and concave interior surface 70. In one exemplary embodiment, second bearing component 16 is made of a relatively rigid material such as metal or ceramic and includes exterior surface 72 having tapered portion 74 adjacent to rim 64. Tapered portion 74 may be used in cooperation with inner surface 92 of conversion ring 80 in a taper-fit manner, so that tapered portion 74 defines a second bearing engagement mechanism.

Conversion ring 80 includes hollow body 82 that extends along axis 83 from first end 84 to second end 86. Conversion ring 80 includes outer surface 88 adapted to engage shell component 12. Outer surface 88 includes annular projection 90 engageable with annular groove 32 of shell component 12. Conversion ring 80 includes tapered inner surface 92 engageable with tapered portion 74 of exterior surface 72 of second bearing component 16, as discussed above, so that inner surface 92 defines an inner ring engagement mechanism. In one exemplary embodiment, conversion ring 80 and second bearing component 16 engage one another in a self-locking taper engagement. In one exemplary embodiment, conversion ring 80 is made of a relatively rigid material, such as metal, to provide rigid support to the relatively rigid second bearing component 16 and to facilitate a tight self-locking taper-fit. In addition to this rigid taper-fit support capability, conversion ring 80 is intraoperatively engageable and disengageable with shell component 12 and second bearing component 16. Thus, intraoperative selection of conversion ring 80, bearing component 16, and shell component 12 is possible as well as intraoperative changing of the components using manual manipulation and readily available tools. Similarly, during a revision surgical procedure, bearing 16, ring 80, and shell 12 may be readily separated to facilitate replacement of bearing 16 and/or ring 80.

In one exemplary embodiment, conversion ring 80 is provided with a plurality of slits 94 cut part-way through body 82 and originating alternately from first and second ends 84, 86 to form a portion of the sidewall into serpentine sidewall 96. In the illustrative conversion ring 80, serpentine sidewall 96 is shown over a small portion of body 82. The serpentine pattern may also be formed in multiple discrete locations around body 82 or it may be formed entirely around body 82. When conversion ring 80 is pressed into shell component 12, slits 94 allow conversion ring 80 to compress to a smaller diameter to permit annular projection 90 to fit through opening 28 and snap into groove 32 to retain second bearing component 16 in shell component 12. A single slit 94 cut all the way through conversion ring 80 may be provided to permit conversion ring 80 to compress. However, multiple alternating slits 94 are advantageous since each slit 94 can be much narrower than would be required by a single slit 94 to provide the same degree of compressibility. By providing multiple narrow slits 94, the localized interruption of inner tapered surface 92 by each slit is minimized. The alternating pattern of slits also provides for continuous, albeit serpentine, support of second bearing component 16 around the entire circumference of conversion ring 80.

Once conversion ring 80 is snapped into shell component 12, conversion ring 80 resiliently expands to abut outer surface 88 of conversion ring 80 against interior surface 26 of shell component 12. This abutment prevents conversion ring 80 from expanding to a larger diameter when second bearing component 16 is inserted into the assembly formed by shell component 12 and conversion ring 80. Likewise, the taper-fit engagement of second bearing component 16 with conversion ring 80 prevents conversion ring 80 from collapsing and exiting shell 12 once second bearing component 16 is engaged with conversion ring 80.

FIGS. 2-3 provide more detailed views of exemplary engagement mechanisms. Snap-fit engagement of first bearing component 14 with shell component 12 is shown in FIG. 2. Engagement of conversion ring 80, second bearing component 16, and shell component 12 to one another is shown in FIG. 3. The taper engagement between second bearing component 16 and conversion ring 80 includes continuous taper surfaces 72, 92 providing support for second bearing component 16 at equatorial rim 64. In one exemplary embodiment, annular projection 90 of conversion ring 80 includes ramped leading edge 100 angling outwardly from outer surface 88 to ease insertion of conversion ring 80 into shell component 12. Seating portion 102 extends from leading edge 100 generally parallel to outer surface 88. Shoulder 104 extends radially inwardly from seating portion 102. Annular groove 32 in shell component 12 has a shape complimentary to annular projection 90. As conversion ring 80 is inserted into shell component 12, ramped leading edge 100 engages opening 28 such that continued axial pressure causes conversion ring 80 to compress and annular projection 90 to slide along inner surface 26 of shell component 12 until projection 90 snaps into annular groove 92. With just conversion ring 80 in shell component 12, conversion ring 80 can be readily pried out of shell component 12. When bearing component 16 is seated in conversion ring 80 it presses conversion ring 80 into engagement with shell component 12 to prevent conversion ring 80 from collapsing and being disengaged with shell component 12. Removal of bearing component 16 again frees conversion ring 80 to be compressed and removed. Preferably, seating portion 102 bottoms in annular groove 32 to form a press fit upon insertion of bearing component 16 to prevent pistoning of conversion ring 80 in shell component 12.

Figure 4:
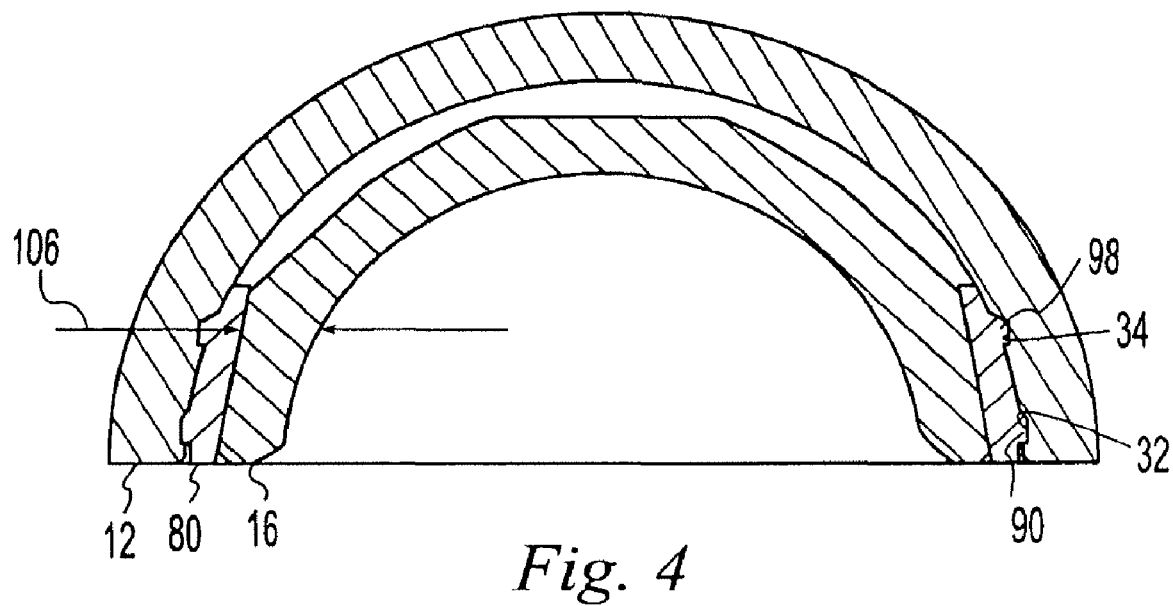
FIG. 4 is an alternative arrangement for the snap-lock mechanism of the acetabular hip component of FIG. 3.

FIG. 4 illustrates an alternative configuration of shell component engagement mechanism 30 of shell component 12 (FIG. 1) comprising second annular groove 34 spaced further axially into shell component 12 from first annular groove 32. In this embodiment, conversion ring 80 may include second annular projection 98 engageable with second annular groove 32 to provide more support for conversion ring 80 and second bearing component 16 (as shown). Alternatively, one of annular grooves 32, 34 may be engaged by first bearing component 14 and the other one of annular grooves 32, 34 may be engaged by conversion ring 80 (not shown). For example, first bearing component 14 may engage annular groove 32 nearer equatorial rim 20 of shell component 12 and conversion ring 80 may engage annular groove 34 that is spaced further from equatorial rim 20 of shell component 12. This arrangement may be advantageous where, for example, first annular groove 32 is positioned to mate with existing bearing components with an annular projection near the equatorial rim and where second annular groove 34 and annular projection 98 of conversion ring 80 are positioned axially inwardly from the equatorial rim to position them near thicker portion 106 of bearing component 16 to support bearing component 16 at thicker portion 106.

In use, an intraoperative decision may be made as to which of alternative bearing components 14, 16 is desired. If first bearing component 14 is to be used, it is snapped directly into shell component 12. If second bearing component 16 is to be used, conversion ring 80 is first snapped into shell component 12 to convert engagement mechanism 30 of shell component 12 from a snap-fit to a taper-fit. Then, second bearing component 16 is pressed into the assembly formed by shell component 12 and conversion ring 80. Conversion ring 80 may be used during a primary hip surgery to allow an intraoperative choice of bearing components 14, 16. Conversion ring 80 may be used during a revision hip surgery to allow a previously implanted bearing component to be replaced by a new bearing component having a different engagement mechanism than the original without having to remove shell component 12. This is desirable, for example, where shell component 12 is firmly fixed in the acetabulum and only the bearing component needs to be changed due to wear or the need for a different bearing configuration, such as a different material, shape, or size. Conversion ring 80 also permits the use of independently designed shell and bearing components, such as a later designed liner with an earlier designed shell or the use of components from distinct design families.

Referring to FIGS. 5-8, another exemplary embodiment of an acetabular cup conversion ring is shown as conversion ring 110. Conversion ring 110 is substantially similar to conversion ring 80, shown in FIGS. 1-4, and identical reference numerals have been used to identify identical or substantially identical parts therebetween. Referring to FIG. 7, conversion ring 110 has an inner diameter ID measured at first end 84, an outer diameter $OD_1$ measured at first end 84, and an outer diameter $OD_2$ measured at second end 86. In exemplary embodiments, inner diameter ID of conversion ring 110 may be as small as 1.2, 1.3, 1.4, 1.5, 1.6, 1.7, 1.8, or 1.9 inches and as large as 2.0, 2.1, 2.2, 2.3, 2.4, 2.5, 2.6, or 2.7 inches, or any diameter within a range defined by any of the foregoing values. Outer diameter $OD_1$ of conversion ring 110 may be as small as 1.4, 1.5, 1.6, 1.7, 1.8, 1.9, or 2.0 inches and as large as 2.1, 2.2, 2.3, 2.4, 2.5, 2.6, 2.7, or 2.8 inches, or any diameter within a range defined by any of the foregoing values. Outer diameter $OD_2$ of conversion ring 110 may be as small as 1.2, 1.3, 1.4, 1.5, 1.6, 1.7, 1.8, or 1.9 inches and as large as 2.0, 2.1, 2.2, 2.3, 2.4, 2.5, 2.6, 2.7, or 2.8 inches, or any diameter within a range defined by any of the foregoing values. Additionally, tapered inner surface 92 of conversion ring 110 defines angle $\gamma$ between diametrically opposed sides of inner surface 92. In one exemplary embodiment, angle $\gamma$ is about 18 degrees. In other exemplary embodiments, angle $\gamma$ may be as small as 15, 16, 17, or 18 degrees and as large as 19, 20, 21, or 22 degrees, or any angle within a range defined by any of the foregoing values.

Figure 5:
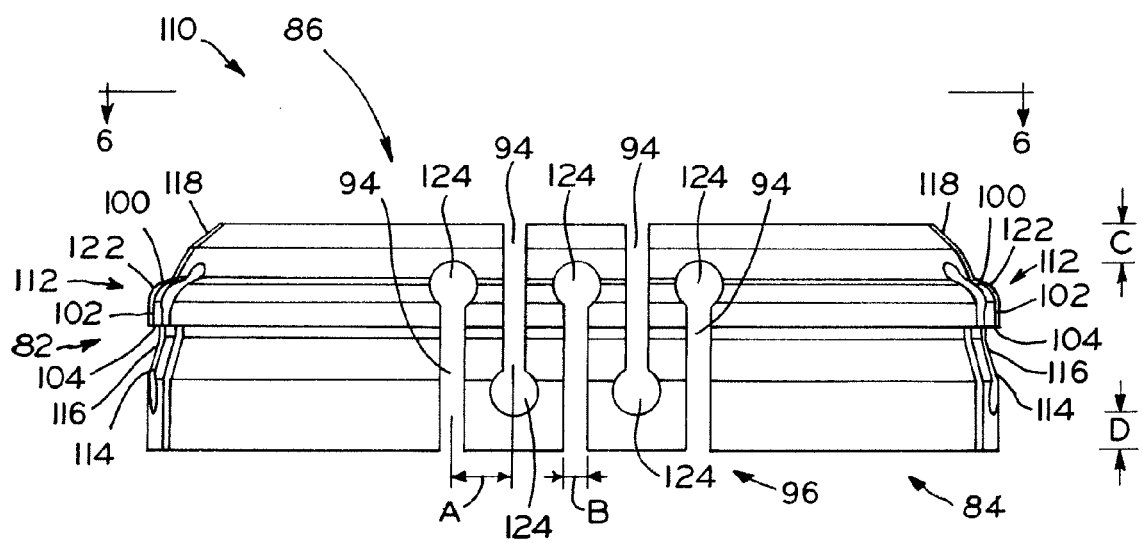
FIG. 5 is an elevational view of an exemplary embodiment of an acetabular cup conversion ring.

Referring to FIGS. 5 and 8, conversion ring 110 includes annular projection 112 having ramped leading edge 100, seating portion 102, and shoulder 104 that are substantially similar to corresponding components of conversion ring 80. In one exemplary embodiment, shown in FIG. 7, ramped leading edge 100 forms angle $\alpha$ with first end 84 of conversion ring 110. In exemplary embodiments, angle $\alpha$ may be as small as 20, 21, 22, 23, 24, or 25 degrees and as large as 26, 27, 28, 29, or 30 degrees, or any angle within a range defined by any of the foregoing values. In one exemplary embodiment, angle $\alpha$ is substantially equal to 26 degrees. In one exemplary embodiment, shoulder 104 is positioned about 0.20 inches from first end 84 of conversion ring 110 and extends for a length of about 0.06 inches. In one exemplary embodiment, the intersection between ramped leading edge 100 and seating portion 102 is defined by radiused portion 122. In one exemplary embodiment, radiused portion 122 has a radius of curvature of about 0.03 inches.

In contrast to conversion ring 80, projection 112 of conversion ring 110 is located closer to second end 86 than annular projection 90 of conversion ring 80. Specifically, in one exemplary embodiment, conversion ring 110 has a height H, shown in FIG. 7, defined between first end 84 and second end 86 of about 0.375 inches and shoulder 104 of annular projection 112 is positioned about 0.21 inches from first end 84 of conversion ring 110. Thus, in this embodiment, shoulder 104 is positioned such that about 56 percent of height H of conversion ring 110 is between shoulder 104 and first end 84, while about 44 percent of height H of conversion ring 110 is between shoulder 104 and second end 86, e.g., projection 112 is positioned closer to second end 86 than first end 84. In other exemplary embodiments, the percentage of height H of conversion ring 110 that is between shoulder 104 and first end 84 may be as low as 50, 55, 60, or 65 percent and as high as 70, 75, 80, or 85 percent, or any percentage value within a range defined by any of the foregoing values. By positioning projection 112 closer to second end 86 than first end 84, sufficient overall support for second bearing component 16 is provided, while still providing sufficient space for anti-rotation features to be formed at the equator of shell component 12.

As shown in FIGS. 5 and 7, positioned adjacent projection 112 in the direction of first end 84 of conversion ring 110 is inwardly tapering ring surface 114. Surface 114 cooperates with shoulder 104 to define recess 116. Recess 116 receives a portion of interior surface 26 of shell component 12, as shown in FIG. 8, when conversion ring 110 is positioned within shell component 12. Conversion ring 110 may also include removal surface 118. Removal surface 118 tapers inwardly in the direction of second end 86. In one exemplary embodiment, removal surface 118 forms an angle β with first end 84 of conversion ring 110.

In exemplary embodiments, angle β may be as small as 40, 41, 42, 43, or 44 degrees and as large as 45, 46, 47, 48, or 49 degrees, or any angle within a range defined by any of the foregoing values. In one exemplary embodiment, removal surface 118 begins about 0.33 inches from first end 84 and continues until it terminates at second end 86.

Removal surface 118 facilitates the removal of conversion ring 110 from shell 12 after projection 112 of conversion ring 110 has been secured within groove 32 of shell 12. Projection 112 of conversion ring 110 may be secured within groove 32 of shell 12 in a substantially similar manner as described in detail above with respect to conversion ring 80. Removal surface 118 cooperates with interior surface 28 of shell component 12 to define gap 120 (FIG. 8). In order to remove conversion ring 110, a removal tool (not shown) is positioned within gap 120 to engage removal surface 118 of conversion ring 110. Once in contact with removal surface 118, a force is applied to the removal tool and, correspondingly, to removal surface 118 and conversion ring 110, that is sufficient to cause conversion ring 110 to compress radially inwardly. For example, as conversion ring 110 is compressed radially inwardly, the distance between the opposing walls of conversion ring 110 that define slits 94, as described in detail below, will be decreased. Once sufficiently compressed, at least a portion of annular projection 112 of conversion ring 110 is positioned outside of groove 32 of shell 12 and conversion ring 110 is then advanced along interior surface 26 of shell 12 in the direction of equitorial rim 20 to remove conversion ring 110 from shell 12. In one exemplary embodiment, a surgeon may grasp conversion ring 110 after annular projection 112 is received within groove 32 of shell 12 and, unassisted, manually apply sufficient force to conversion ring 110 to remove conversion ring 110 from shell 12.

Figure 6:
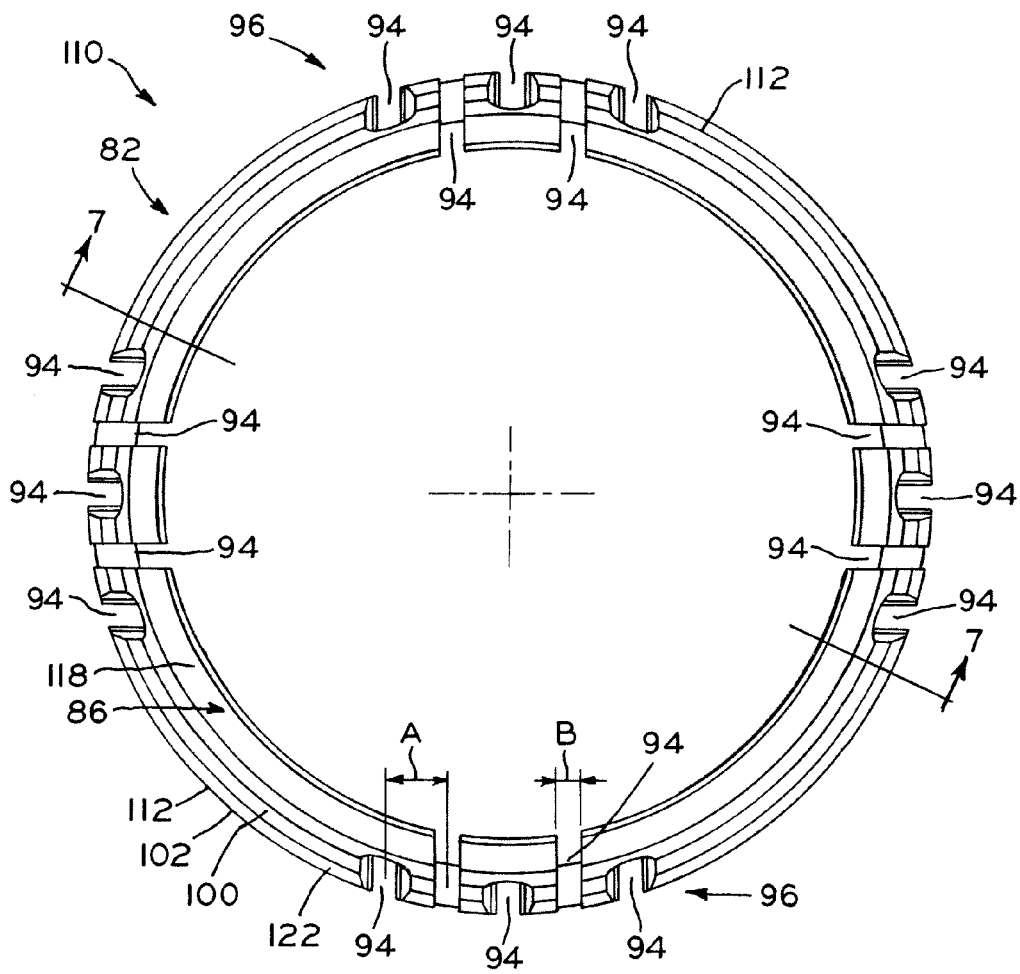
FIG. 6 is a plan view of the conversion ring of FIG. 5 viewed in the direction of arrows 6-6 of FIG. 5.

Referring to FIGS. 5 and 6, conversion ring 110 includes slits 94 that define serpentine sidewall 96, as described in detail above with respect to conversion ring 80. Serpentine sidewall 96 and conversion ring 110 includes a plurality of slits 94 that are spaced from another by a distance A, as measured between the longitudinal axes of adjacent slits 94. In one exemplary embodiment, distance A is about 0.10 inches. Additionally, each of slits 94 have a longitudinal width B. In one exemplary embodiment, width B is equal to about 0.04 inches. Each of slits 94 also terminates at radiused terminal ends 124. In one exemplary embodiment, radiused terminal ends 124 have a radius of about 0.02 inches.

As discussed above with respect to conversion ring 80, slits 94 do not extend entirely through hollow body 82 of conversion ring 110. Specifically, each of slits 94 that extend through first end 84 terminate adjacent to second end 86 of conversion ring 110, but are spaced a distance away from second end 86. In one exemplary embodiment, slits 94 that extend through first end 84 have terminal ends 124 that are spaced from second end 86 by a distance C, shown in FIG. 5, which, in one exemplary embodiment, is about 0.04 inches. Similarly, each of slits 94 that extend through second end 86 terminate adjacent first end 84 of conversion ring 110, but are spaced a distance away from first end 84. In one exemplary embodiment, slits 94 that extend through second end 86 have terminal ends 124 that are spaced from first end 84 by a distance D, shown in FIG. 5, which, in one exemplary embodiment, is about 0.06 inches.

Referring to FIG. 6, conversion ring 110 includes four separate sets of slits 94, each set having two slits 94 extending through second end 86 and terminating adjacent to first end 84 and three slits 94 extending through first end 84 and terminating adjacent to second end 86. Thus, a total of eight slits 94 are provided around body 82 of conversion ring 110 that extend through second end 86 and a total of twelve slits 94 are provided around body 82 of conversion ring 110 that extend through first end 84.

Referring to FIG. 9, another exemplary embodiment of conversion ring 110 is shown that has six separate sets of slits 94, each set having two slits 94 extending through second end 86 and terminating adjacent to first end 84 and three slits 94 extending through first end 84 and terminating adjacent to second end 86. As a result, a total of twelve slits 94 are provided around body 82 of conversion ring 110 that extend through second end 86 and a total of eighteen slits 94 are provided around body 82 of conversion ring 110 that extend through first end 84. In one exemplary embodiment, each of the sets of slits 94 are positioned to extend around conversion ring 110 at equally spaced distances. Thus, in the embodiment shown in FIG. 9, three sets of slits 94 are positioned on one half of conversion ring 110 and the remaining three sets of slits 94 are positioned on the other half of conversion ring 110.

By utilizing six sets of slits 94, each having two slits extending through second end 86 and terminating adjacent first end 84 and three slits extending through first end 84 and terminating adjacent second end 86, in conjunction with the design of projection 112 described in detail above, conversion ring 110 may have an average insertion force, i.e., the force required to insert conversion ring 110 through opening 28 in shell component 12 and advance conversion ring 110 until annular projection 112 seats within annular groove 32, as small as 50, 55, 60, or 65 pounds and as high as 70, 75, 80, or 85 pounds, or any force within a range defined by any of the foregoing values. However, the average insertion force required to insert any particular conversion ring 110 into a corresponding shell 12 may be dependent, in part, on the selection of the specific variable dimensions identified above with respect to conversion ring 110. In one exemplary embodiment, a surgeon may grasp conversion ring 110 and, unassisted, manually apply a sufficient force to conversion ring 110 to advance conversion ring 110 into shell 12 until projection 112 is received within annular groove 32.

Although examples of an acetabular cup conversion ring and its use have been described and illustrated in detail herein, it is to be understood that the same is intended by way of illustration and example only and is not to be taken by way of limitation. The invention has been illustrated in use to convert a snap-fit shell engagement mechanism to a taper-fit shell engagement mechanism. However, the acetabular cup conversion ring may be configured to convert any shell engagement mechanism into any other shell engagement mechanism. Accordingly, variations in and modifications to the acetabular cup conversion ring and its use will be apparent to those of ordinary skill in the art, and the following claims are intended to cover all such modifications and equivalents.

What is claimed is:

1. An acetabular prosthesis comprising:
   a shell component having a convex external surface shaped for engagement with an acetabulum and a concave interior surface defining an internal cavity, said interior surface including an annular groove;

a first bearing component having a convex external surface and a concave internal surface, said external surface of said first bearing component defining an annular projection configured for receipt within said annular groove of said shell component in mating snap-fit engagement;

a conversion ring having a sidewall defining an outer surface and a tapered inner surface, said sidewall extending axially from a first end to a second end, said outer surface defining an annular projection configured for receipt within said annular groove of said shell component in mating snap-fit engagement; and a second bearing component having a tapered external surface and a concave internal surface, said external surface of said second bearing component configured to releasably engage said tapered inner surface of said conversion ring in mating taper-fit engagement, wherein said projection of said conversion ring further comprises a ramped leading edge, a seating portion, and a shoulder, said seating portion extending substantially parallel to said outer surface of said conversion ring, and an angle $\alpha$ extending between said leading edge of said conversion ring and said first end of said conversion ring, said angle $\alpha$ being greater than or equal to 20 degrees and less than or equal to 30 degrees.

2. The acetabular prosthesis of claim 1, wherein said first bearing component is formed from a polymer and said second bearing component is formed from one of a metal and a ceramic.

3. The acetabular prosthesis of claim 1, wherein said angle $\alpha$ is equal to about 26 degrees.

4. An acetabular prosthesis comprising:

a shell component having a convex external surface shaped for engagement with an acetabulum and a concave interior surface defining an internal cavity, said interior surface including an annular groove;

a first bearing component having a convex external surface and a concave internal surface, said external surface of said first bearing component defining an annular projection configured for receipt within said annular groove of said shell component in mating snap-fit engagement;

a conversion ring having a sidewall defining an outer surface and a tapered inner surface, said sidewall extending axially from a first end to a second end, said outer surface defining an annular projection configured for receipt within said annular groove of said shell component in mating snap-fit engagement; and a second bearing component having a tapered external surface and a concave internal surface, said external surface of said second bearing component configured to releasably engage said tapered inner surface of said conversion ring in mating taper-fit engagement, wherein said conversion ring further comprises a plurality of slits extending at least half-way and less than entirely through said sidewall between said first and second ends, wherein adjacent slits alternately originate from said first and second ends to form said sidewall into a serpentine sidewall.

5. The acetabular prosthesis of claim 4, wherein adjacent ones of said plurality of slits are separated by a distance of about 0.10 inches.

6. The acetabular prosthesis of claim 4, wherein each of said plurality of slits has a width of about 0.04 inches.

7. The acetabular prosthesis of claim 4, wherein each of said plurality of slits has a radiused terminal end.

8. An acetabular prosthesis comprising:

a shell component having a convex external surface shaped for engagement with an acetabulum and a concave interior surface defining an internal cavity, said interior surface including an annular groove;

a first bearing component having a convex external surface and a concave internal surface, said external surface of said first bearing component defining an annular projection configured for receipt within said annular groove of said shell component in mating snap-fit engagement;

a conversion ring having a sidewall defining an outer surface and a tapered inner surface, said sidewall extending axially from a first end to a second end, said outer surface defining an annular projection configured for receipt within said annular groove of said shell component in mating snap-fit engagement; and a second bearing component having a tapered external surface and a concave internal surface, said external surface of said second bearing component configured to releasably engage said tapered inner surface of said conversion ring in mating taper-fit engagement, wherein said conversion ring further comprises a removal surface tapering inwardly toward said second end of said conversion ring, and an angle $\beta$ defined between said removal surface and said first end of said conversion ring, said angle $\beta$ being equal to or less than 50 degrees, wherein, with said conversion ring received within said shell component, a gap is defined between said interior surface of said shell component and said removal surface of said conversion ring.

9. The acetabular prosthesis of claim 1, wherein said projection of said conversion ring extends from said outer surface of said conversion ring at a position that is closer to said second end of said conversion ring than said first end of said conversion ring.

10. An acetabular prosthesis comprising:

a shell component having a convex external surface shaped for engagement with an acetabulum and a concave interior surface defining an internal cavity, said interior surface including an annular groove;

a first bearing component having a convex external surface and a concave internal surface, said external surface of said first bearing component defining an annular projection configured for receipt within said annular groove of said shell component in mating snap-fit engagement;

a conversion ring having a sidewall defining an outer surface and a tapered inner surface, said sidewall extending axially from a first end to a second end, said outer surface defining an annular projection configured for receipt within said annular groove of said shell component in mating snap-fit engagement; and a second bearing component having a tapered external surface and a concave internal surface, said external surface of said second bearing component configured to releasably engage said tapered inner surface of said conversion ring in mating taper-fit engagement, wherein an angle $\gamma$ is defined between diametrically opposed ends of said tapered inner surface of said conversion ring, said angle $\gamma$ being greater than or equal to 15 degrees and less than or equal to 22 degrees.

11. The acetabular prosthesis of claim 10, wherein said angle $\gamma$ is equal to about 18 degrees.

12. A kit of acetabular components for assembling an acetabular joint prosthesis, the kit comprising:

a shell component having an external surface shaped for engagement with an acetabulum and an internal cavity, said cavity including a shell component engagement mechanism;

a first bearing component having an external surface, said external surface of said first bearing component defining a complimentary first bearing engagement mechanism engageable with said shell component engagement mechanism;

a conversion ring having a sidewall defining an outer surface and an inner surface and extending axially from a first end to a second end, said outer surface defining a complimentary outer ring engagement mechanism releasably engageable with said shell component engagement mechanism, said inner surface defining an inner ring engagement mechanism;

a second bearing component having an external surface, said external surface of said second bearing component defining a complimentary second bearing engagement mechanism releasably engageable with said inner ring engagement mechanism, such that said conversion ring is insertable into said shell component to convert said shell component from a first shell/bearing engagement mechanism to a second shell/bearing engagement mechanism, said first and second shell/bearing engagement mechanisms being of different types selected from the group consisting of snap-fit, press-fit, taper-fit, and threaded-fit engagement mechanisms, wherein said shell component engagement mechanism comprises a snap-fit and said external surface of said first bearing component and said external surface of said conversion ring each include a resilient portion for snapping into said shell component, wherein said second shell/bearing engagement mechanism comprises a taper-fit and said inner surface of said conversion ring defines a tapered surface such that said conversion ring is intraoperatively engageable with said shell to convert said shell from a snap-fit to a taper-fit engagement mechanism, wherein said snap-fit mechanism comprises an annular projection formed on each of said first bearing component and said conversion ring and a first annular groove and a second annular groove formed in said shell, said first annular groove and said second annular groove being spaced apart axially with said second annular groove being further into said shell than said first annular groove, said first bearing component comprising an annular projection engageable with said first annular groove and said conversion ring comprising an annular projection engageable with said second annular groove.

13. The kit of claim 12, wherein said first bearing component comprises a polymer body, said external surface of said first bearing component engageable with said internal cavity of said shell, said external surface of said first bearing component including a flexible shell engagement portion and said second bearing component comprises a rigid non-polymeric body having a rigid external surface, said rigid external surface defining a tapered engagement surface.

14. A kit of acetabular components for assembling an acetabular joint prosthesis, the kit comprising:
a shell component having an external surface shaped for engagement with an acetabulum and an internal cavity, said cavity including a shell component engagement mechanism;

a first bearing component having an external surface, said external surface of said first bearing component defining a complimentary first bearing engagement mechanism engageable with said shell component engagement mechanism;

a conversion ring having a sidewall defining an outer surface and an inner surface and extending axially from a first end to a second end, said outer surface defining a complimentary outer ring engagement mechanism releasably engageable with said shell component engagement mechanism, said inner surface defining an inner ring engagement mechanism;

a second bearing component having an external surface, said external surface of said second bearing component defining a complimentary second bearing engagement mechanism releasably engageable with said inner ring engagement mechanism, such that said conversion ring is insertable into said shell component to convert said shell component from a first shell/bearing engagement mechanism to a second shell/bearing engagement mechanism, said first and second shell/bearing engagement mechanisms being of different types selected from the group consisting of snap-fit, press-fit, taper-fit, and threaded-fit engagement mechanisms, wherein said shell component engagement mechanism comprises a snap-fit and said conversion ring is resiliently collapsible upon insertion into said shell to engage said snap-fit mechanism.

15. A kit of acetabular components for assembling an acetabular joint prosthesis, the kit comprising:
a shell component having an external surface shaped for engagement with an acetabulum and an internal cavity, said cavity including a shell component engagement mechanism;

a first bearing component having an external surface, said external surface of said first bearing component defining a complimentary first bearing engagement mechanism engageable with said shell component engagement mechanism;

a conversion ring having a sidewall defining an outer surface and an inner surface and extending axially from a first end to a second end, said outer surface defining a complimentary outer ring engagement mechanism releasably engageable with said shell component engagement mechanism, said inner surface defining an inner ring engagement mechanism;

a second bearing component having an external surface, said external surface of said second bearing component defining a complimentary second bearing engagement mechanism releasably engageable with said inner ring engagement mechanism, such that said conversion ring is insertable into said shell component to convert said shell component from a first shell/bearing engagement mechanism to a second shell/bearing engagement mechanism, said first and second shell/bearing engagement mechanisms being of different types selected from the group consisting of snap-fit, press-fit, taper-fit, and threaded-fit engagement mechanisms, wherein said sidewall includes a plurality of slits extending part-way through said sidewall between said first and second ends, adjacent slits alternately originating from said first and second ends to form said sidewall into a serpentine sidewall.

16. The acetabular prosthesis of claim 4, wherein said first bearing component is formed from a polymer and said second bearing component is formed from one of a metal and a ceramic.

17. The acetabular prosthesis of claim 4, wherein said projection of said conversion ring further comprises a ramped leading edge, a seating portion, and a shoulder, said seating portion extending substantially parallel to said outer surface of said conversion ring, and an angle α extending between said leading edge of said conversion ring and said first end of said conversion ring, said angle α being greater than or equal to 20 degrees and less than or equal to 30 degrees.

18. The acetabular prosthesis of claim 17, wherein said angle α is equal to about 26 degrees.

19. The acetabular prosthesis of claim 4, wherein said conversion ring further comprises a removal surface tapering inwardly toward said second end of said conversion ring, and an angle β defined between said removal surface and said first end of said conversion ring, said angle β being equal to or less than 50 degrees, wherein, with said conversion ring received within said shell component, a gap is defined between said interior surface of said shell component and said removal surface of said conversion ring.

20. The acetabular prosthesis of claim 4, wherein an angle γ is defined between diametrically opposed ends of said tapered inner surface of said conversion ring, said angle γ being greater than or equal to 15 degrees and less than or equal to 22 degrees.

* * * * *